United States Patent
Trezza et al.

(10) Patent No.: US 10,918,790 B2
(45) Date of Patent: Feb. 16, 2021

(54) DUAL SYRINGE WITH FUNNEL FEEDING KIT

(71) Applicants: Guangzhou Bioseal Biotech Co., Ltd., Guangzhou Science City (CN); Ethicon, Inc., Somerville, NJ (US)

(72) Inventors: Michael J. Trezza, Long Valley, NJ (US); John Goodman, Ann Arbor, MI (US)

(73) Assignees: Guangzhou Bioseal Biotech Co., Ltd., Guangzhou (CN); Ethicon, Inc., Somerville, NJ (US)

( * ) Notice: Subject to any disclaimer, the term of this patent is extended or adjusted under 35 U.S.C. 154(b) by 251 days.

(21) Appl. No.: 15/623,791

(22) Filed: Jun. 15, 2017

(65) Prior Publication Data

US 2018/0361065 A1    Dec. 20, 2018

(51) Int. Cl.
  *A61M 5/19*   (2006.01)
  *A61B 17/00*  (2006.01)
  *A61M 5/315*  (2006.01)
  *A61M 5/32*   (2006.01)

(52) U.S. Cl.
  CPC ......... *A61M 5/19* (2013.01); *A61B 17/00491* (2013.01); *A61M 5/31511* (2013.01); *A61M 5/3286* (2013.01); *A61M 5/3295* (2013.01); *A61B 2017/00495* (2013.01); *A61B 2017/00522* (2013.01); *A61M 2205/19* (2013.01); *A61M 2209/084* (2013.01)

(58) Field of Classification Search
  CPC .. A61M 5/19; A61M 5/31511; A61M 5/3286; A61M 5/3295; A61M 11/00; A61M 5/3298; A61M 5/3294; A61M 5/2448; A61M 5/284; A61B 2017/00495; B05C 17/00553
  See application file for complete search history.

(56) References Cited

U.S. PATENT DOCUMENTS

| | | | |
|---|---|---|---|
| 5,116,315 A | | 5/1992 | Capozzi et al. |
| 5,290,259 A | | 3/1994 | Fischer |
| 5,376,079 A | | 12/1994 | Holm |
| 5,456,388 A | | 10/1995 | Honstein et al. |
| 5,605,255 A | * | 2/1997 | Reidel ................ B05B 7/10 222/137 |
| 5,957,937 A | * | 9/1999 | Yoon .................. A61B 17/0469 606/144 |

(Continued)

OTHER PUBLICATIONS

International search report and written opinion dated Sep. 5, 2018, for PCT/IB2018/054164.

*Primary Examiner* — Brandy S Lee
*Assistant Examiner* — Nidah M Hussain
(74) *Attorney, Agent, or Firm* — David R. Crichton; Leo B. Kriksunov

(57) ABSTRACT

The present invention is directed to multi-liquid loading and delivery kits comprising a first storage vessel for a first active component, a second storage vessel for a second active component, at least two transfer syringes, at least two vial adaptors, at least two cannulas with a through lumen and a multi-liquid delivery device. The delivery device has dual hollow cartridges, each with at least one throughbore at one end and plunger access at the opposing end, a kick stand, a removable dual feed funnel, a spray or drip manifold and at least one spray or drip tip assembly.

14 Claims, 23 Drawing Sheets

(56) References Cited

U.S. PATENT DOCUMENTS

| | | | |
|---|---|---|---|
| 6,063,055 A | 5/2000 | Epstein et al. | |
| 6,116,900 A | 9/2000 | Ostler | |
| 6,132,396 A | 10/2000 | Antanavich et al. | |
| 6,290,101 B1 | 9/2001 | Chung | |
| 6,610,033 B1 | 8/2003 | Melanson et al. | |
| 6,716,195 B2 | 4/2004 | Nolan, Jr. et al. | |
| 7,635,343 B2 * | 12/2009 | McIntosh | A61B 17/00491 |
| | | | 604/82 |
| D653,325 S | 1/2012 | Cheesman et al. | |
| 8,240,511 B2 | 8/2012 | Greter et al. | |
| 8,417,320 B2 | 4/2013 | Martz | |
| 8,419,722 B2 | 4/2013 | Richards et al. | |
| 8,506,547 B2 | 8/2013 | Sharratt et al. | |
| 8,974,424 B2 | 3/2015 | Kaisha | |
| 9,131,930 B2 | 9/2015 | Greter | |
| 9,174,001 B2 | 11/2015 | Kirk et al. | |
| 9,220,846 B2 | 12/2015 | Jones et al. | |
| 9,333,303 B2 | 5/2016 | Leak et al. | |
| 2003/0120212 A1 | 6/2003 | Dedig et al. | |
| 2006/0196885 A1 * | 9/2006 | Leach | A61M 11/06 |
| | | | 222/82 |
| 2013/0312868 A1 * | 11/2013 | Ilan | B01F 5/0685 |
| | | | 141/4 |
| 2013/0325059 A1 | 12/2013 | O'Neill | |
| 2013/0331658 A1 | 12/2013 | Kai et al. | |
| 2014/0074154 A1 | 3/2014 | Goodman et al. | |
| 2014/0114276 A1 * | 4/2014 | Schweiss | B01F 15/0201 |
| | | | 604/416 |
| 2017/0202743 A1 * | 7/2017 | Wu | A61J 1/2003 |

\* cited by examiner

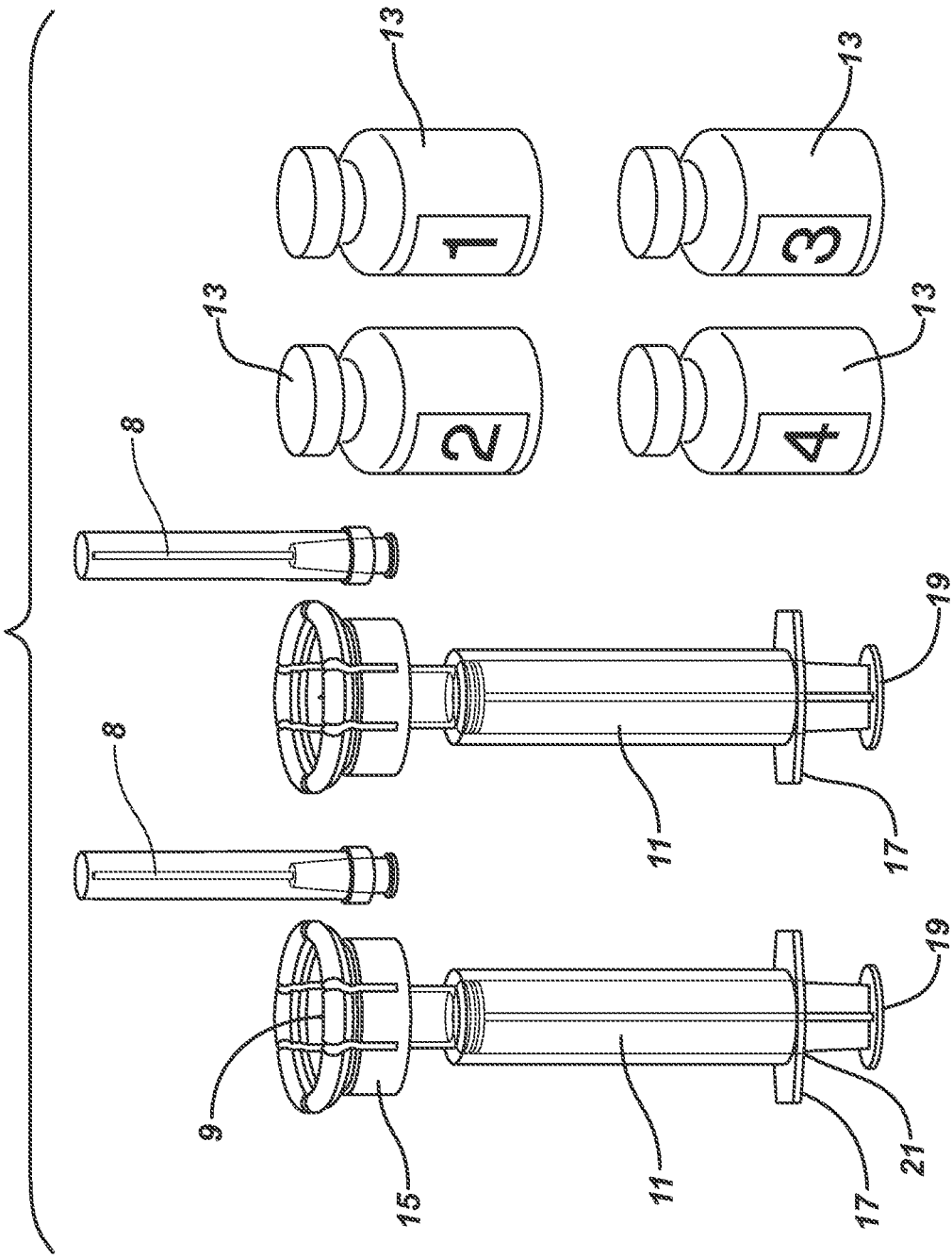

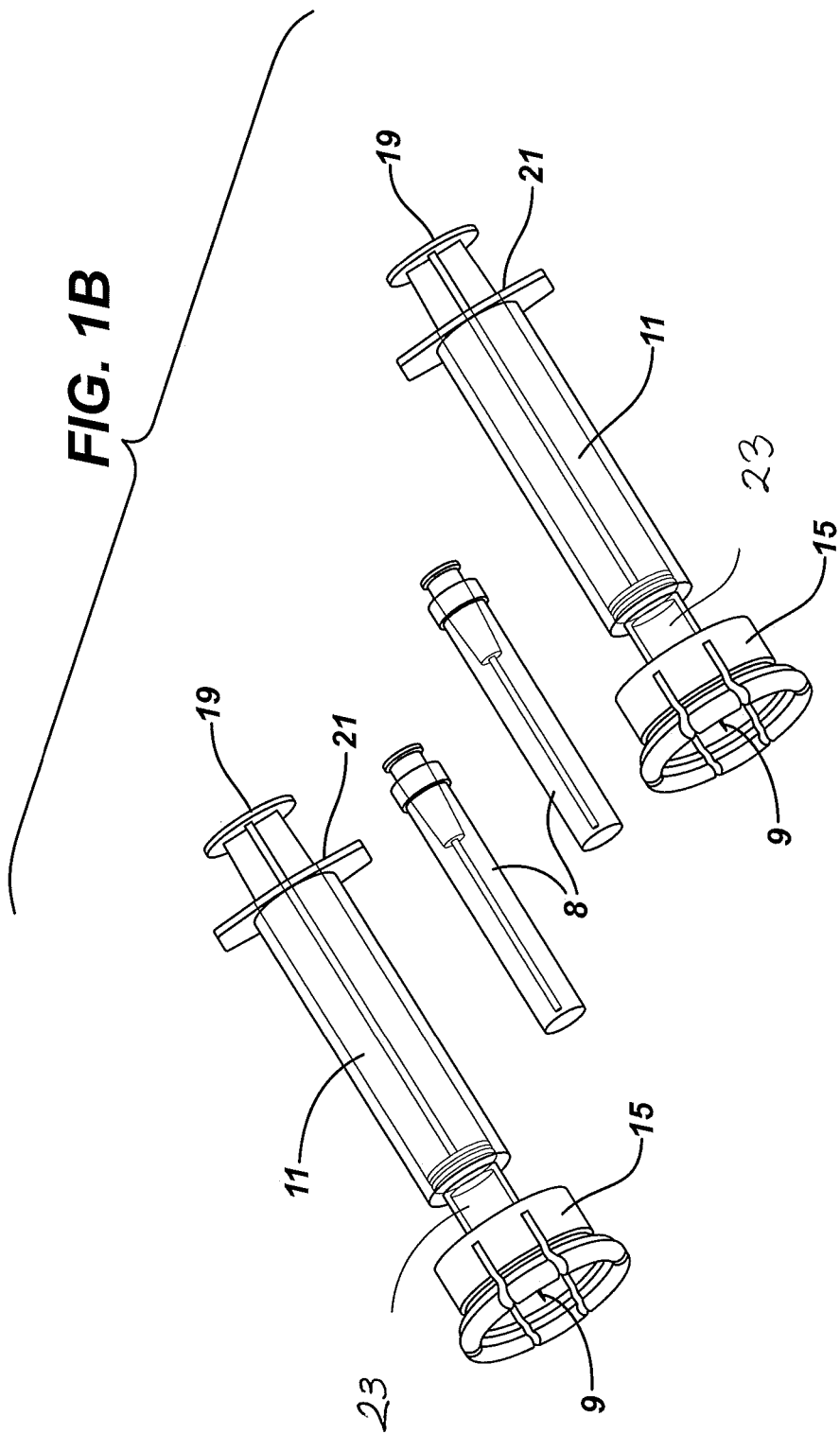

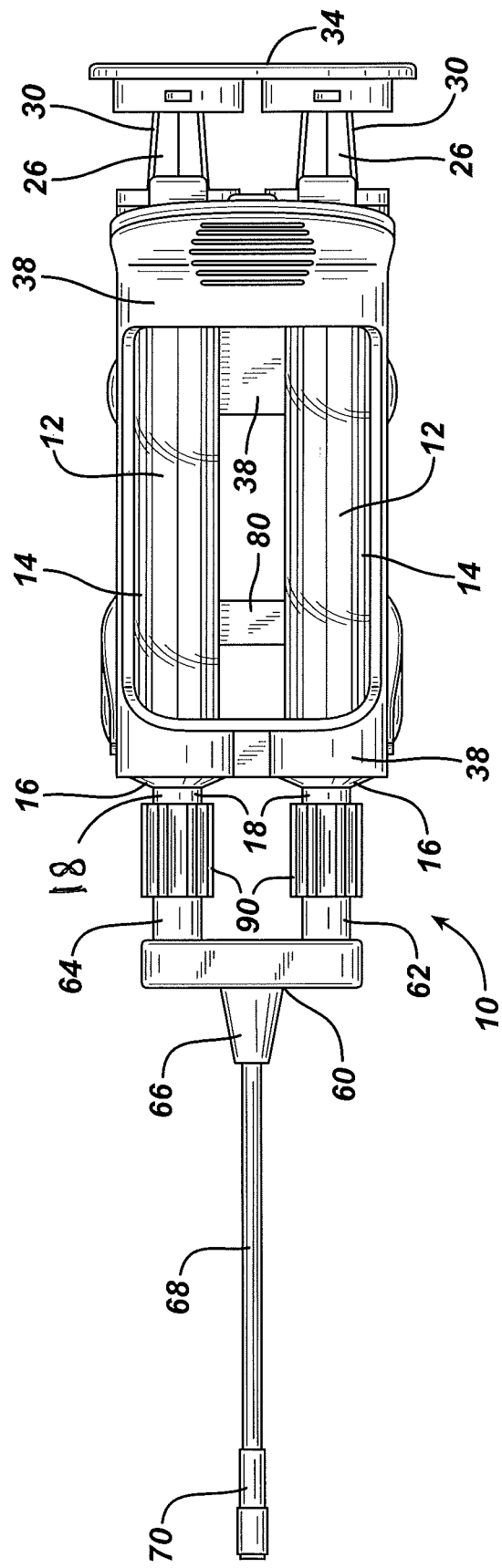

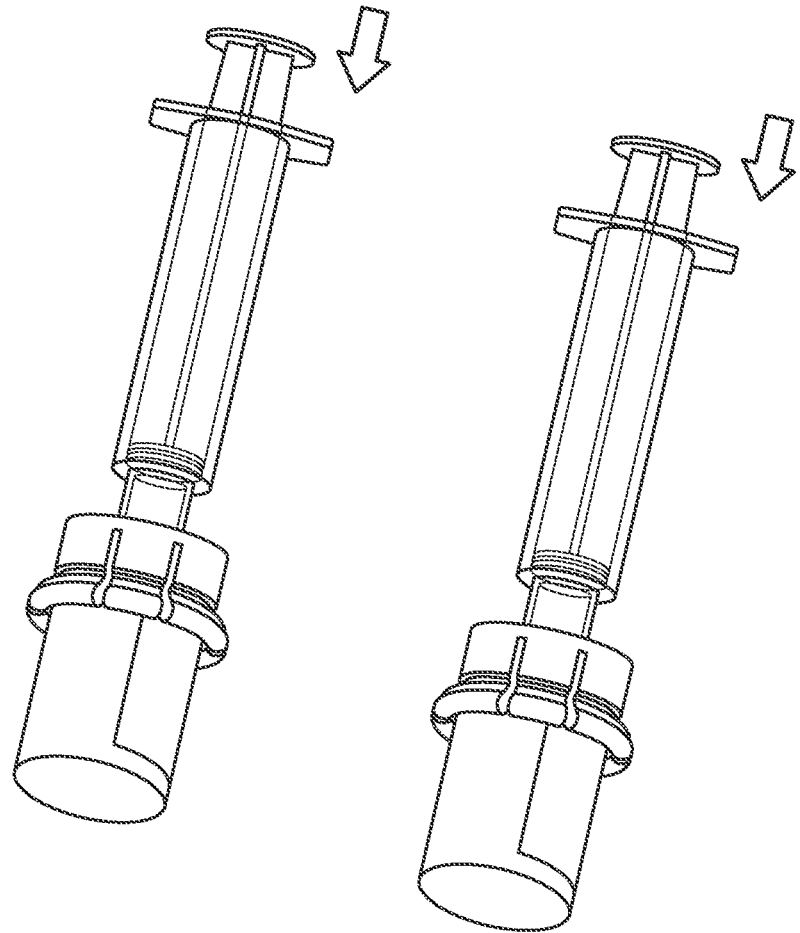

DUAL SYRINGE WITH FUNNEL FEEDING KIT

BACKGROUND OF THE INVENTION

The present disclosure relates to methods, devices and kits for transferring fluids from storage and reconstitution vessels to a delivery device in a surgical environment such as an operating room.

BACKGROUND

Drip devices for dispensing two or more biocomponents are known. In the medical device field, such devices are typically used for applying bioadhesives, polymers and other synthetic material used in wound closure. Because of the reactant nature of the biocomponents used to form the bioadhesive, mixing of the components does not occur until the solution is ready to be applied. Mixing of the components too soon before application may result in the premature polymerization reaction or hardening of the mixture, thereby making application of the solution impossible. Thus, in known drip devices, the two or more components are maintained separately until just prior to application. The drip devices may include one or more pre-mixing means for mixing the two or more solutions prior to application. The pre-mixing means may be passive, i.e., spiral configuration in the tubing, or instead may be active, i.e., mixing blade or impeller. Once mixed, the solution may be applied through a needle-like output or may instead be ejected through a spray assembly.

An exemplary device is taught in U.S. Pat. No. 5,116,315, entitled "Biological Syringe System", which discloses a system for delivery two fluids in a mixed composition, comprising a manifold and a discharge assembly. The discharge assembly mixes fluids in a mixing space and then atomizes the mixed fluids in a spray delivered from the assembly. Similarly, the device shown in U.S. Pat. No. 5,605,255, entitled, "Apparatus for Spraying a mixture of Two Components', is an apparatus for spraying a liquid mixture having two syringes, a connecting piece, a premixing chamber, and a reduced volume section downstream from premixing chamber, and an exit aperture for spraying the mixture. The reduced volume section terminates in a homogenization region. U.S. Pat. No. 6,063,055, entitled "Turbulence Mixing Head for a Tissue Sealant Applicator and Spray Head for Same", illustrates a device in which the mixing is performed in a mixing head.

U.S. Pat. No. 6,132,396, titled "Apparatus for applying tissue sealant" discloses a manifold for combining first and second components of a material, comprising a body having first and second inlet ports, a tubular dispenser coupled to the body and provided with an outlet and an internal passageway in fluid communication with said outlet, said body having first fluid transport means adapted for transporting said first component from said first inlet port to said internal passageway and second fluid transport means adapted for transporting said second component from said second inlet port to said internal passageway, said first fluid transport means including a hypodermic needle in fluid connection with said first inlet port and having an outlet disposed within said internal passageway, said second fluid transport means including a channel in the body and in fluid connection with said second inlet port and provided with an outlet disposed within said internal passageway the hypodermic needle is located in or able to penetrate the channel whereby said first and second components are directed by said first and second transport means into said tubular dispenser for mixing prior to discharge from the outlet of said tubular dispenser.

U.S. Patent Application Publication No. 2013/0325059 titled "Non-Clogging Airless Spray for High Viscosity, High Surface Tension Fluids" discloses a medical device for spraying two liquids comprised of a first and second syringe each syringe having an outlet for a first and second liquid; a connecting piece having first and second channels in communication with said syringe outlets terminating in distal component comprised of a spray cap which contain independent fluid passages for said first and second liquids and a first and second exit surface; wherein first and second exit surfaces of said spray cap contain a plurality of small exit apertures and said first and second exit apertures create a spray pattern which combines and mixes said first and second liquids away from the device.

U.S. Pat. No. 8,506,547 is directed to a method and device for transferring fluids from a non-sterile field to a sterile field within a surgical environment utilizing a device that includes a main body having a first inlet port that is in communication with a first outlet port. Fluid is taken from the patient, typically with a sterile syringe and transferred to the non-sterile field where the fluid is processed. The processed fluid is then drawn into another syringe in the non-sterile field and a distal end of the first syringe is place within the inlet port of the sterile main body. A distal end of a second sterile syringe is inserted into the outlet port, where the distal ends of the sterile syringe and the non-sterile syringe do not make contact. As a plunger is forced into a chamber of the first non-sterile syringe to force the fluid out of the first syringe, the plunger of the second sterile syringe is retracted such that a chamber in the second syringe has a sufficient volume to store the processed liquid. Since the first non-sterile syringe and the second sterile syringe do not make contact during the transfer of the processed fluid, the sterile field is maintained and the fluid can be utilized in the surgical procedure.

SUMMARY OF THE INVENTION

The present invention is directed to multi-liquid loading and delivery kits comprising a first storage vessel for a first active component, a second storage vessel for a second active component, at least two transfer syringes, at least two vial adaptors, at least two cannulas with a through lumen and a multi-liquid delivery device. The delivery device has dual hollow cartridges, each with at least one throughbore at one end and plunger access at the opposing end, a kick stand, a removable dual feed funnel, a spray manifold with interchangeable spray tips and one drip tip assembly. In one embodiment, each cannula is constructed from flexible material and is provided with blunt non-traumatic end tip.

In one aspect, there is provided a multi-liquid loading and delivery kit comprising:
  a) A first storage vessel for a first active component;
  b) A second storage vessel for a second active component;
  c) At least two transfer syringes;
  d) At least two vial adaptors;
  e) At least two cannulas with a through lumen; and
  f) A multi-liquid delivery device comprising:
    a. dual hollow cartridges, each with at least one throughbore at one end and plunger access at an opposing end;
    b. a kick stand, e.g., a rotatable kick stand;

c. a removable dual feed funnel;
d. a spray manifold; and
e. at least one spray or drip tip assembly.

In some embodiments, the removable dual feed funnel is interchangeable with the spray manifold.

In some embodiments, each cannula is flexible and is provided with a blunt nontraumatic end tip. In some embodiments, the at least one spray tip assembly comprises a spray cartridge with a dual path opening, an interior mixing region, an atomizing insert and flexible spray outlet cover.

In some embodiments, the at least one drip tip assembly comprises a drip cartridge with a dual path opening in fluid communication via channels with a flexible drip outlet. In some embodiments, the kit further comprises at least one reconstituting vessel containing a solubilizing liquid.

The spray tip assembly can be constructed from multiple elements including a manifold with a dual path opening, an interior mixing region and an atomizing insert. Alternatively, the drip tip assembly can include a manifold with a dual path opening in fluid communication via channels with a flexible drip outlet. The spray tip assembly can be directly attached to the manifold or connected via a multi-lumen, flexible tube to the spray manifold.

The first and second components are in solid form, preferably as active ingredients, more preferably as hemostatically active components. Hemostatically active components means, for purposes of this application, components that activate clotting forming agents or once activated by another active component form clots when exposed to blood or blood plasma derivatives. At least one of the components can be stored in a vial as a lyophilized powder. In one embodiment, the first component is thrombin and the second component is a hemostatically active extract from blood plasma, more preferably, the second component is fibrinogen. The reconstituting vials preferably contain a liquid capable of solubilizing the first and second components, such as an aqueous solution or a buffered solution containing a calcium salt.

The present invention also relates to methods for using the kit described above by placing the reconstitution set on a table, transferring the delivery device from the packaging into a sterile field, preparing a first solution, preparing a second solution, retracting the plungers of the dual-syringe system to a predetermined position, rotating the kick stand into the open position, inserting the end of first and second cannula through first and second funnels of the barrel for each cartridge in the dual-syringe system, replacing the funnel with a manifold and attaching a dispensing tip to the manifold. The first and second solutions are prepared analogously by inserting a vial adaptor on a reconstitution syringe into a vial containing a dissolving solution, drawing the dissolving solution into a syringe, replacing the dissolving solution vial on the adaptor with a first active vial, injecting the dissolving solution into the active vial, withdrawing the active containing solution into the first syringe and replacing the vial adaptor with a first cannula.

BRIEF DESCRIPTION OF THE DRAWINGS

FIG. 1A is a schematic top view of the reconstitution tools and sterile fluid transfer device.

FIG. 1B is a perspective view of the reconstitution tools and sterile fluid transfer device.

FIG. 6 is a top view of the sterile delivery device in spray mode with funnel, a mixing and spraying manifold, and non-retracted plungers.

DETAILED DESCRIPTION OF ILLUSTRATIVE EMBODIMENTS

Figure 2A:
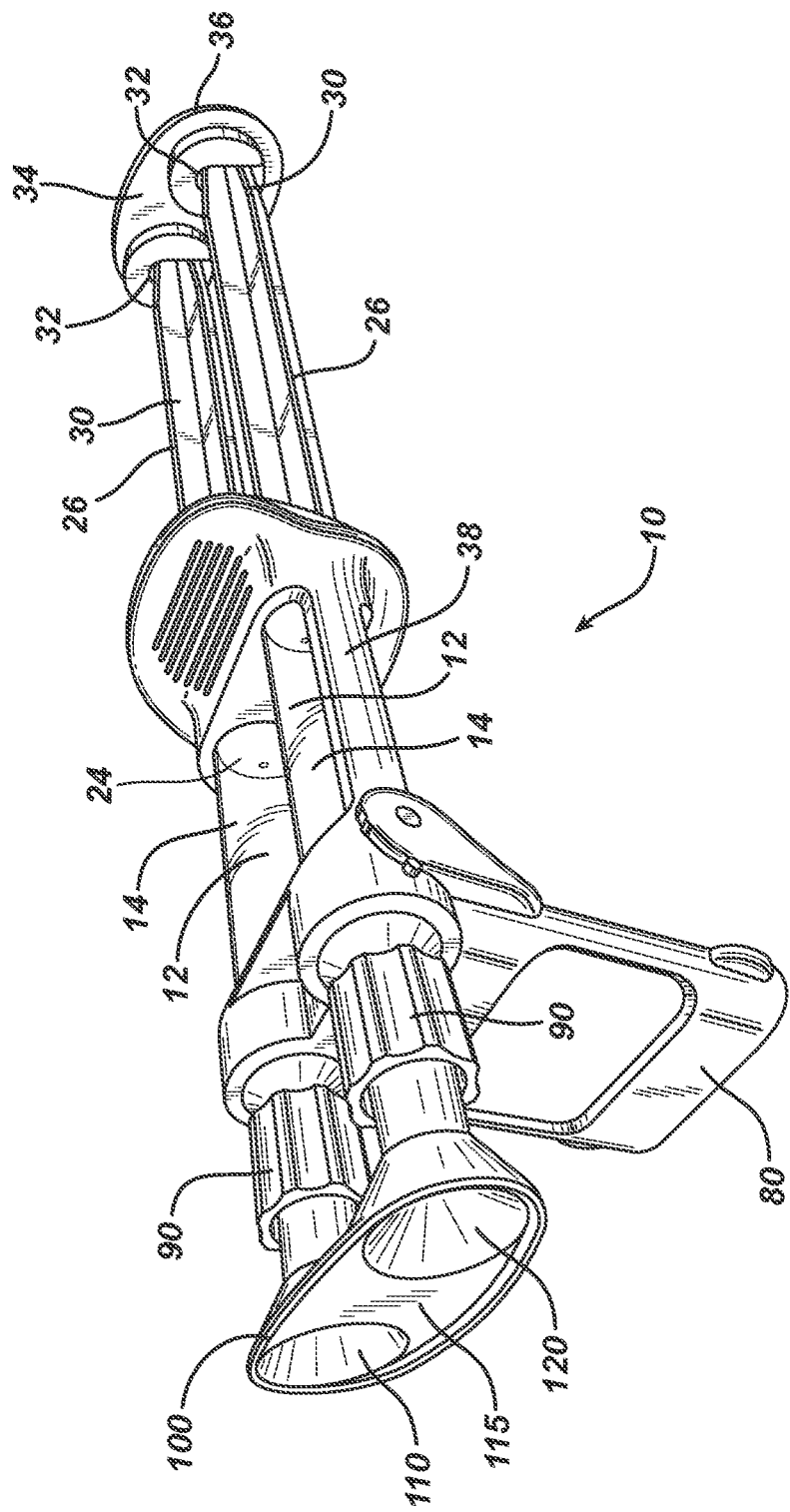
FIG. 2A is a perspective view of the sterile delivery device in transfer mode as viewed from the top in a filling position with deployed kickstand, attached funnel, and retracted plungers.
Figure 2B:
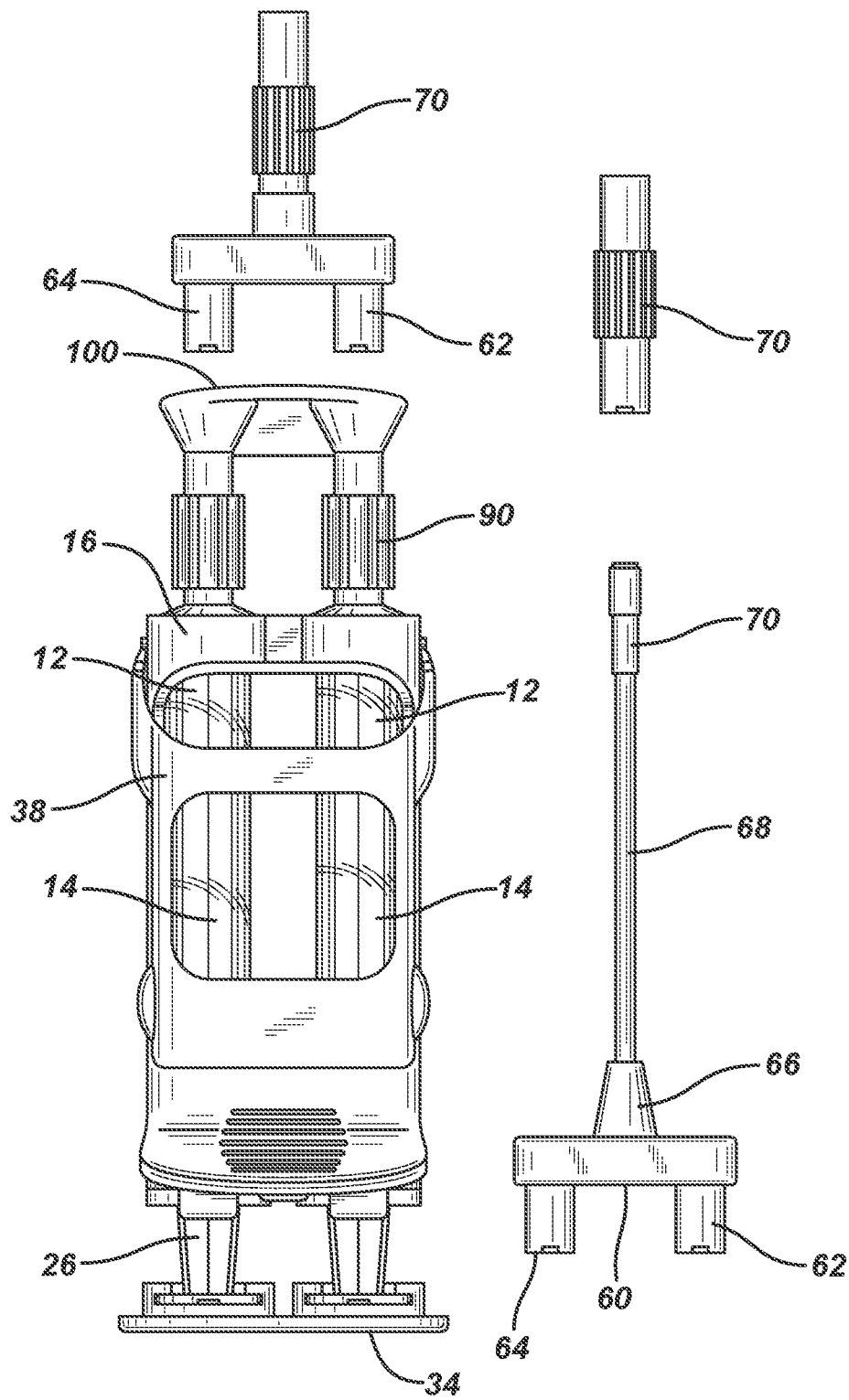
FIG. 2B is a schematic top view of the delivery device with funnel attached, non-retracted plungers, a manifold with spray tip, extra spray tip, and manifold with drip tip.
Figure 3:
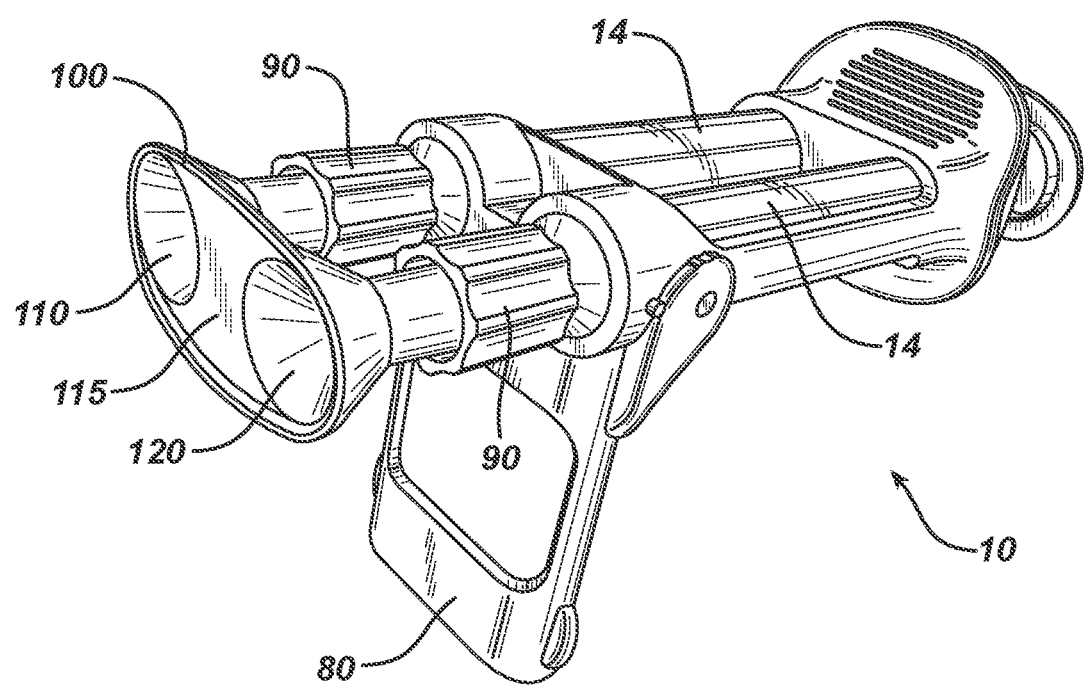
FIG. 3 is a perspective view of the sterile delivery device in transfer mode with deployed kickstand, attached funnel, and non-retracted plungers.
Figure 4:
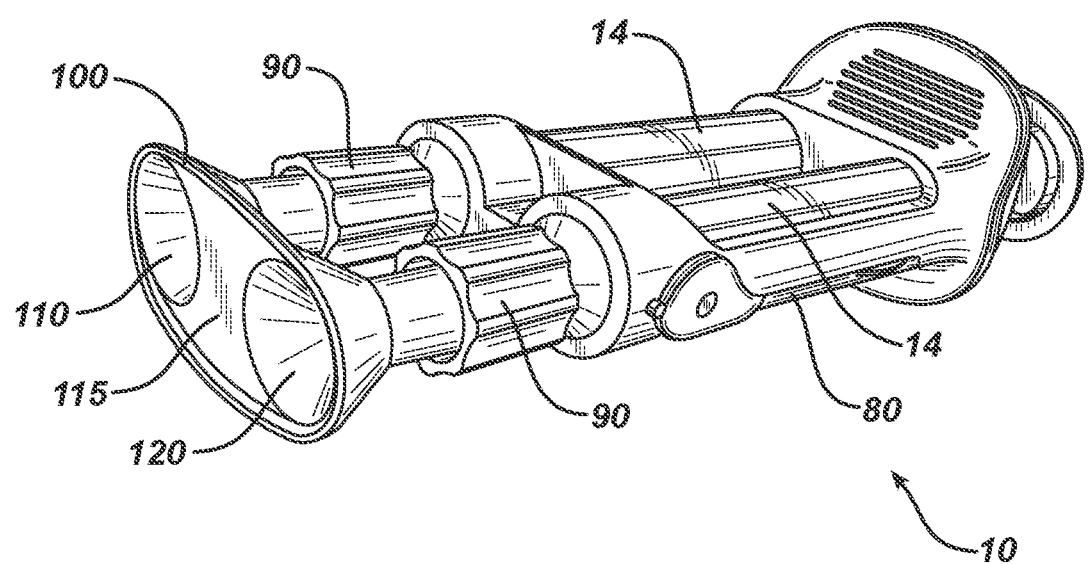
FIG. 4 is a perspective view of the sterile delivery device in transfer mode with retracted kickstand, attached funnel, and non-retracted plungers.

The present invention relates to a method, a device and a kit for transferring fluids from storage and reconstitution vessels to a delivery device in a surgical environment such as an operating room. Reconstitution tools and storage vessels are generally illustrated in FIGS. 1A and 1B, while delivery device 10 in transfer mode is shown in FIGS. 2-4 and in delivery or drip mode in FIGS. 5-6. Delivery device 10 in FIG. 2B has at least two syringes that are set in a dual syringe configuration, where the delivery device 10 and the syringes can be packaged individually or together in a kit with the delivery device 10.

A set of reconstitution tools are shown in FIG. 1A consisting of a pair of loading syringes 11, corresponding storage vials 13 (1-4) and spike adaptors 15. Storage vials 13(1) and (2), in one embodiment, contain substantially dry active components, preferably lyophilized proteins or plasma derived components. Storage vials 13(3) and (4), in the first embodiment, contain reconstitution solutions, such as saline or buffered aqueous solutions. Each loading syringe 11 is a hollow cylindrical tube with handles 17, an outlet 23 at an end distal to handles 17 and a plunger arm 19 that fits snuggly within the interior space of loading syringe 11 though an opening 21 in said handle 17. Retracting plunger arm 19 creates empty space between the base of plunger arm 19 and outlet 23 for loading syringe 11. Spike adaptors 15 are configured to accept vials 13 and simultaneously pierce vial septum with spikes 9. Sterile, non-metallic cannulas 8 are provided for subsequent transfer of reconstituted materials drawn into syringes 11 into delivery device 10.

Figure 5:
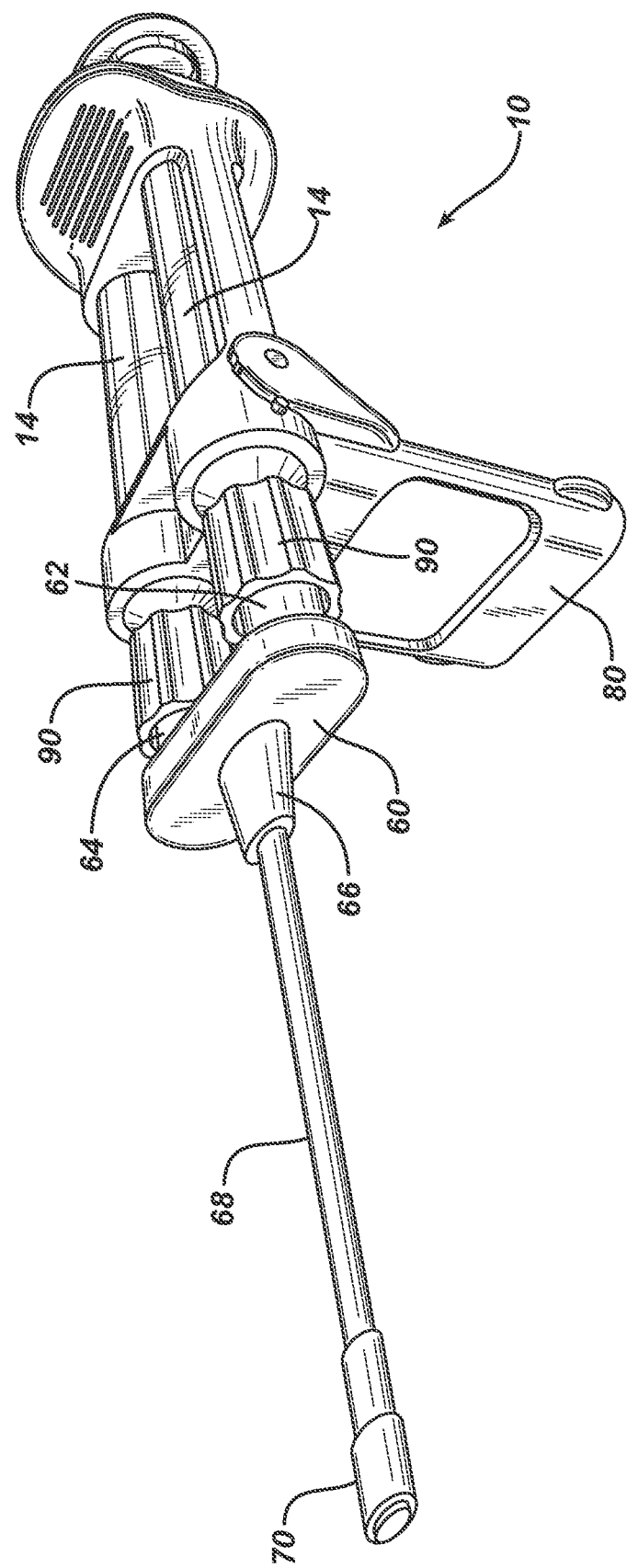
FIG. 5 is a perspective view of the sterile delivery device in drip mode with deployed kickstand, a drip tip, and non-retracted plungers.
Figure 7A:
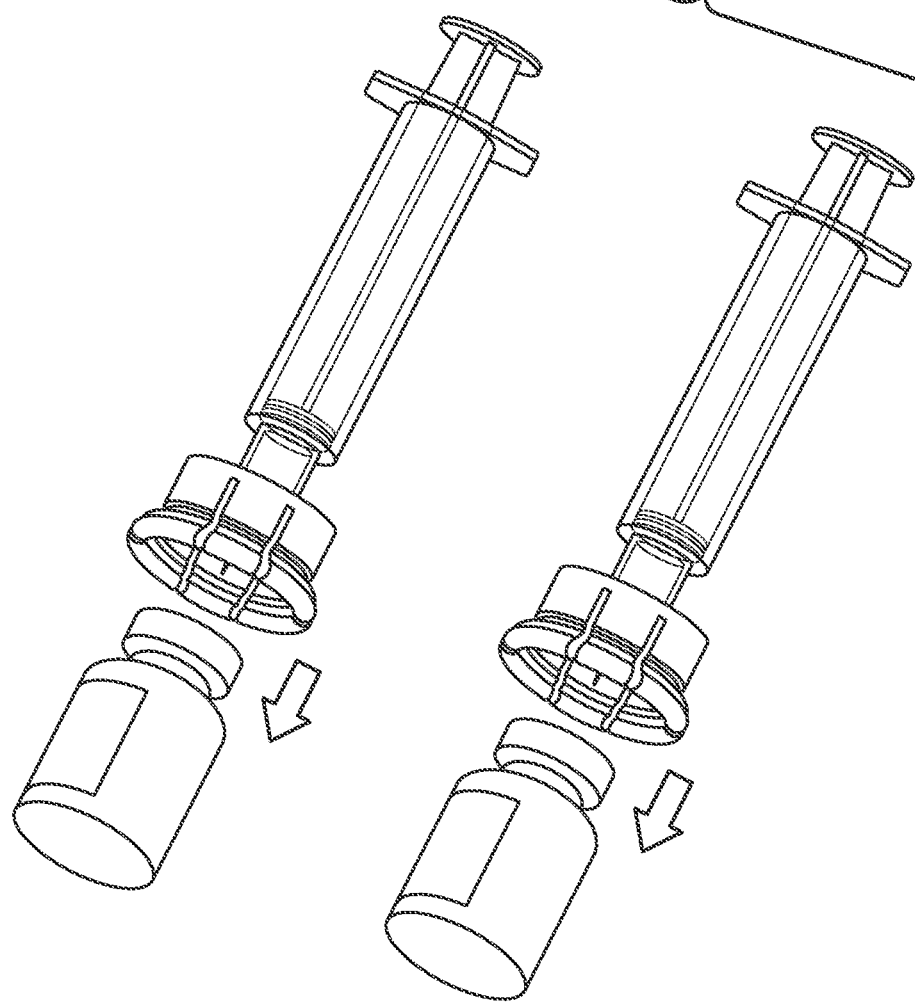
FIGS. 7A-7O are diagrams showing operational process steps for the inventive kit and devices.
Figure 7B:
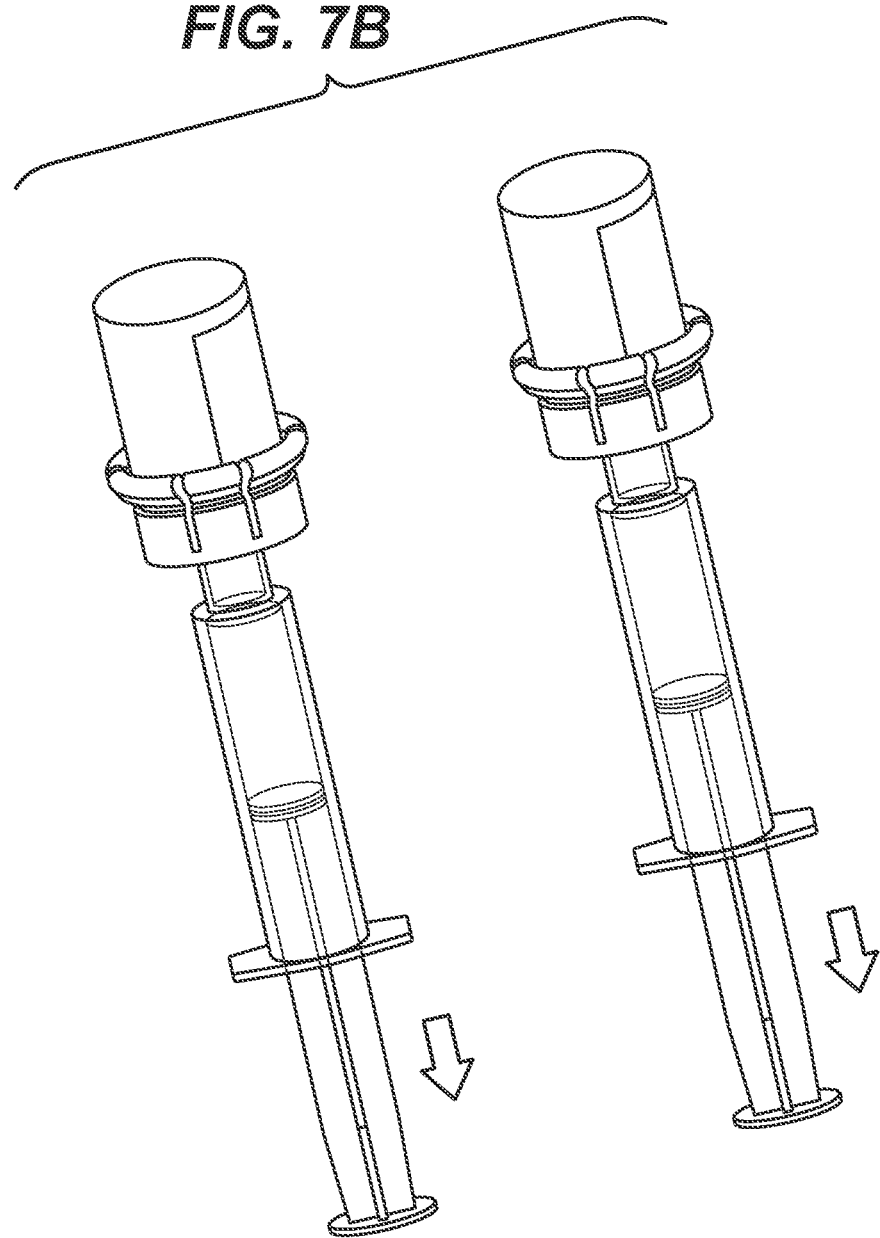
Figure 7C:
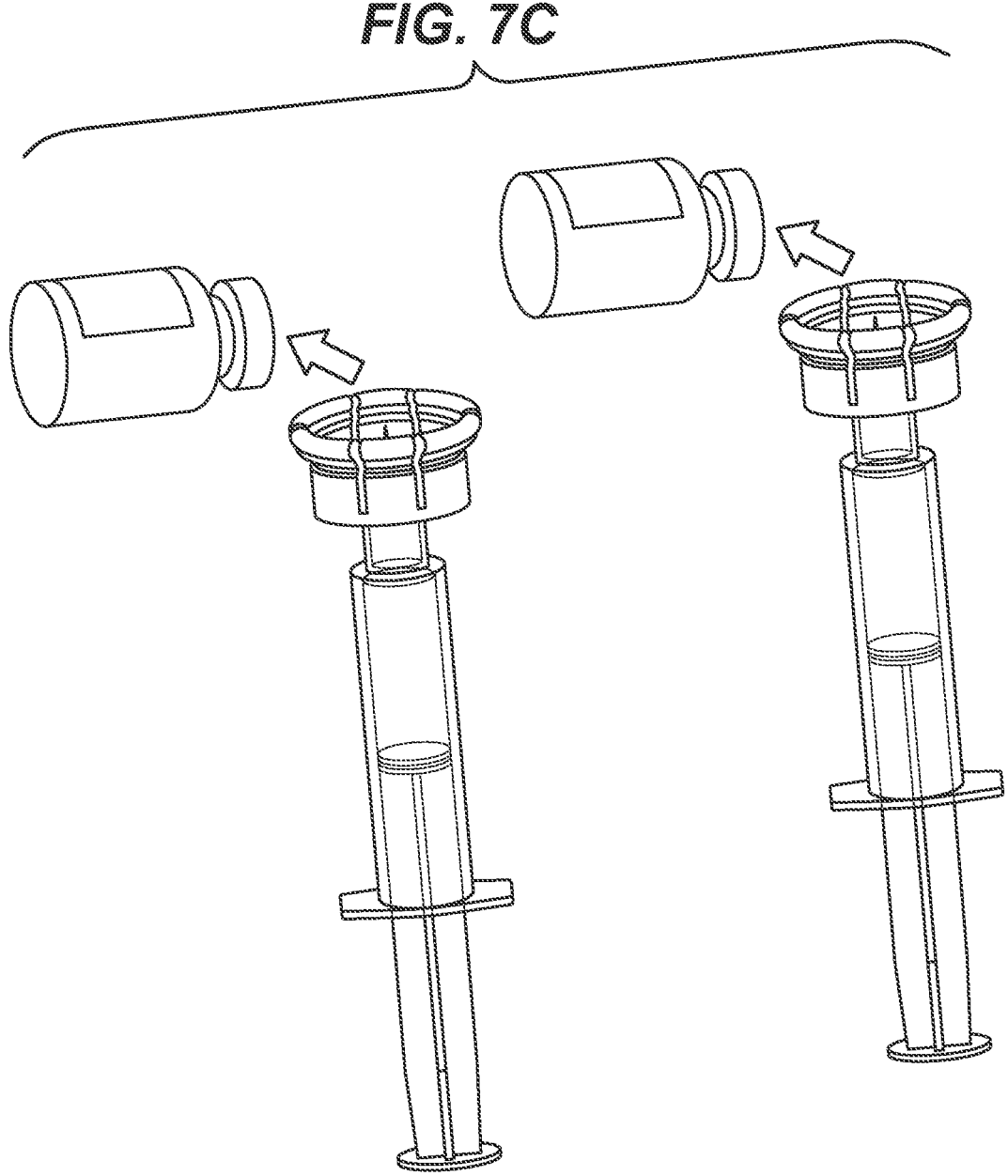
Figure 7D:
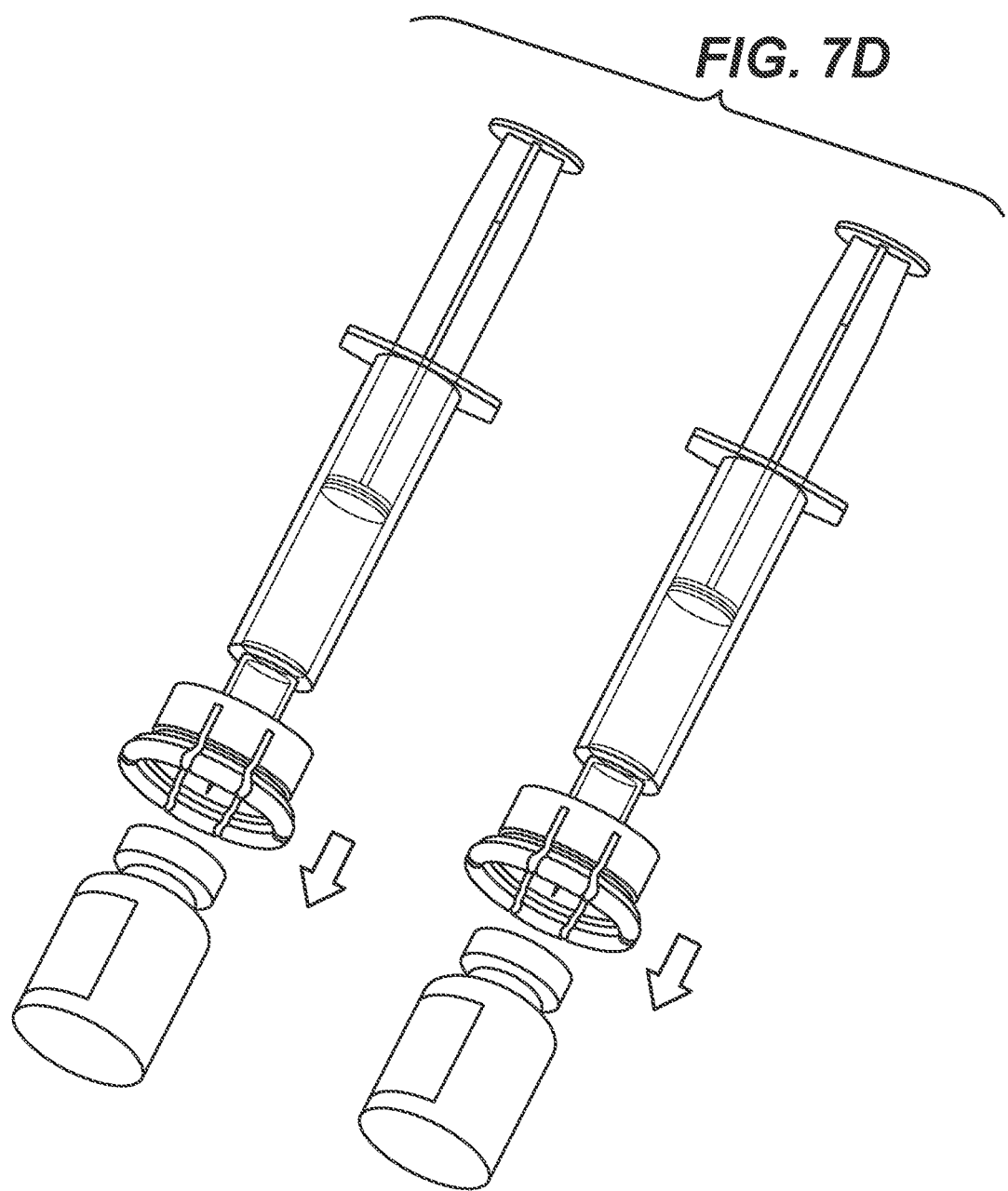
Figure 7F:
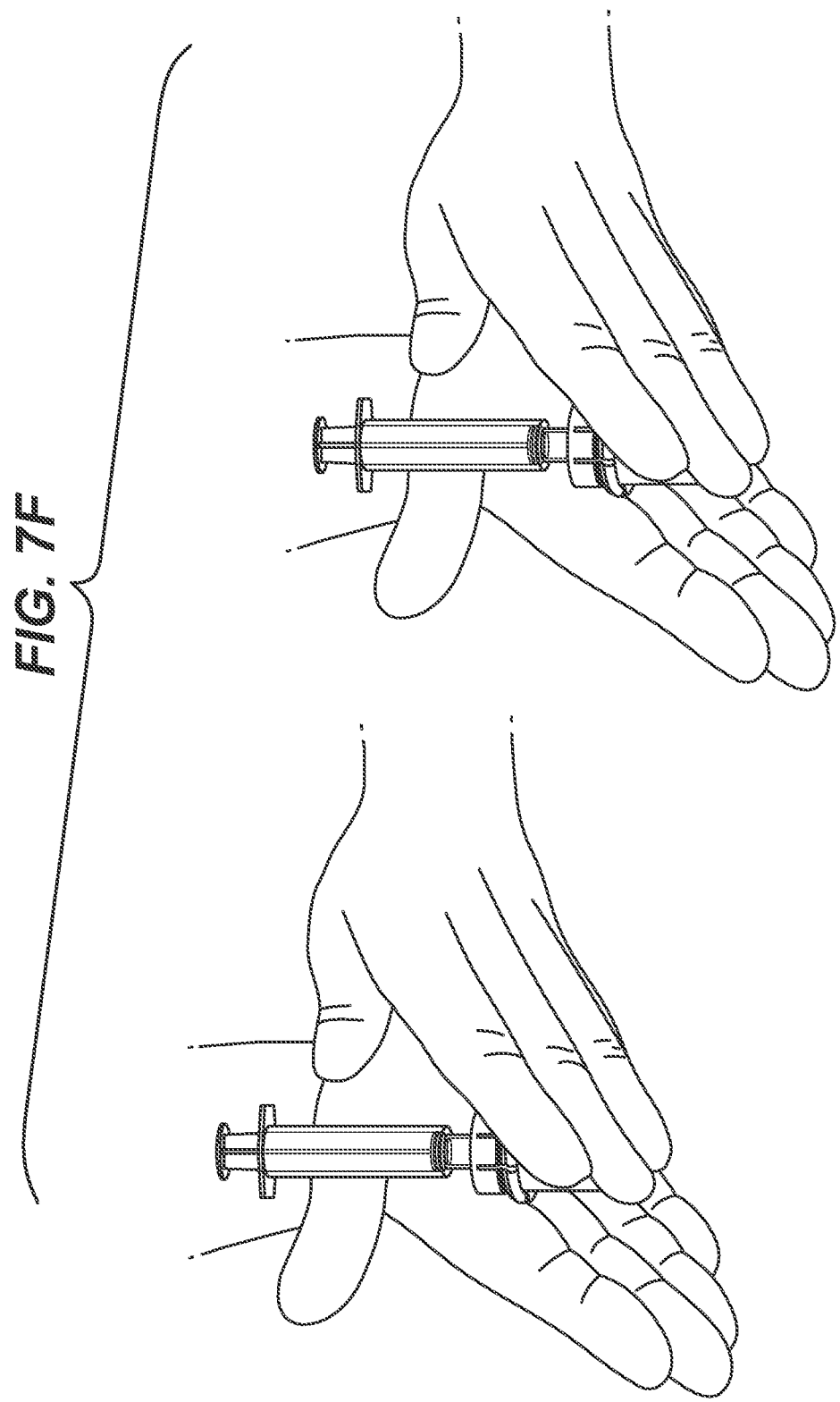
Figure 7G:
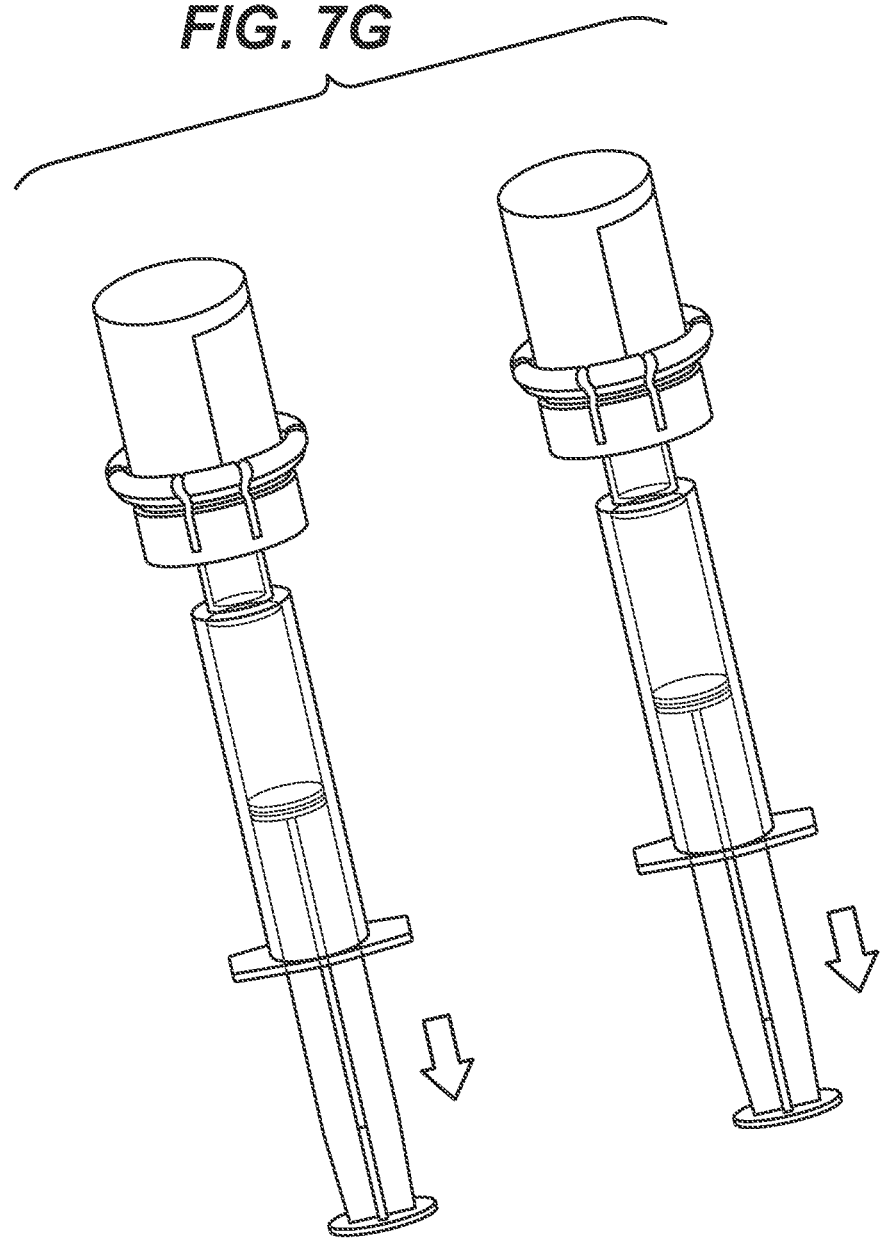
Figure 7H:
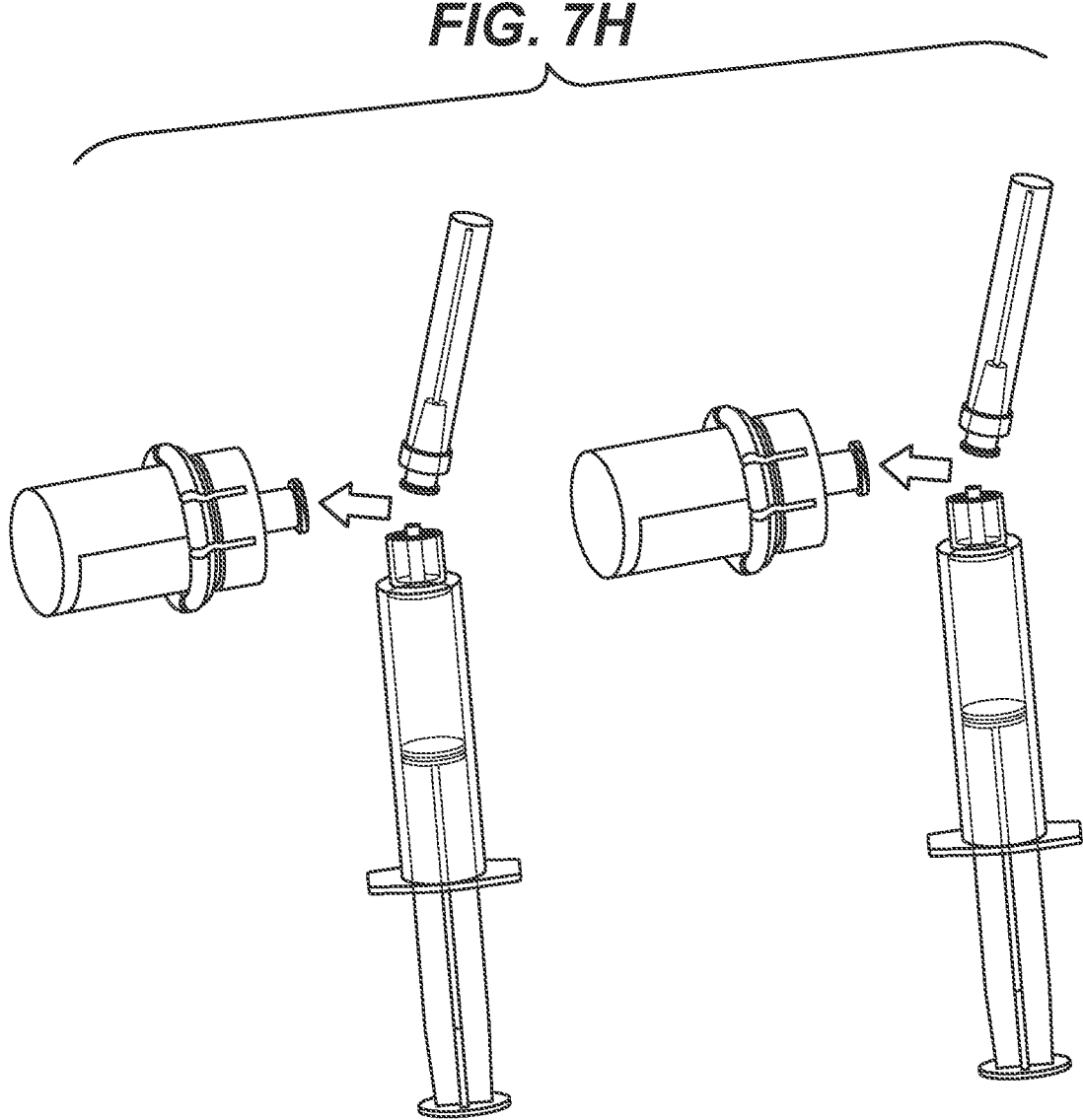
Figure 71:
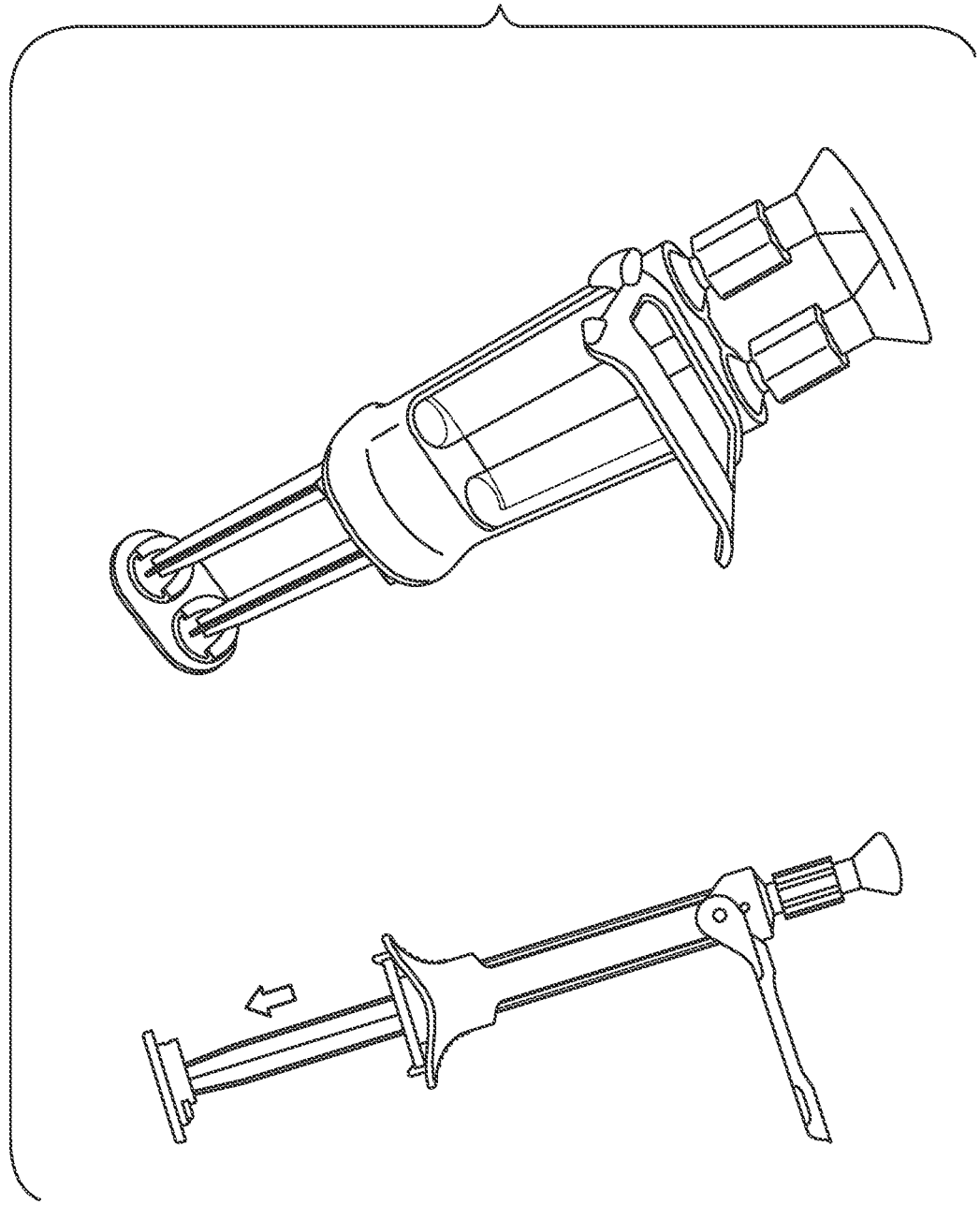
Figure 7J:
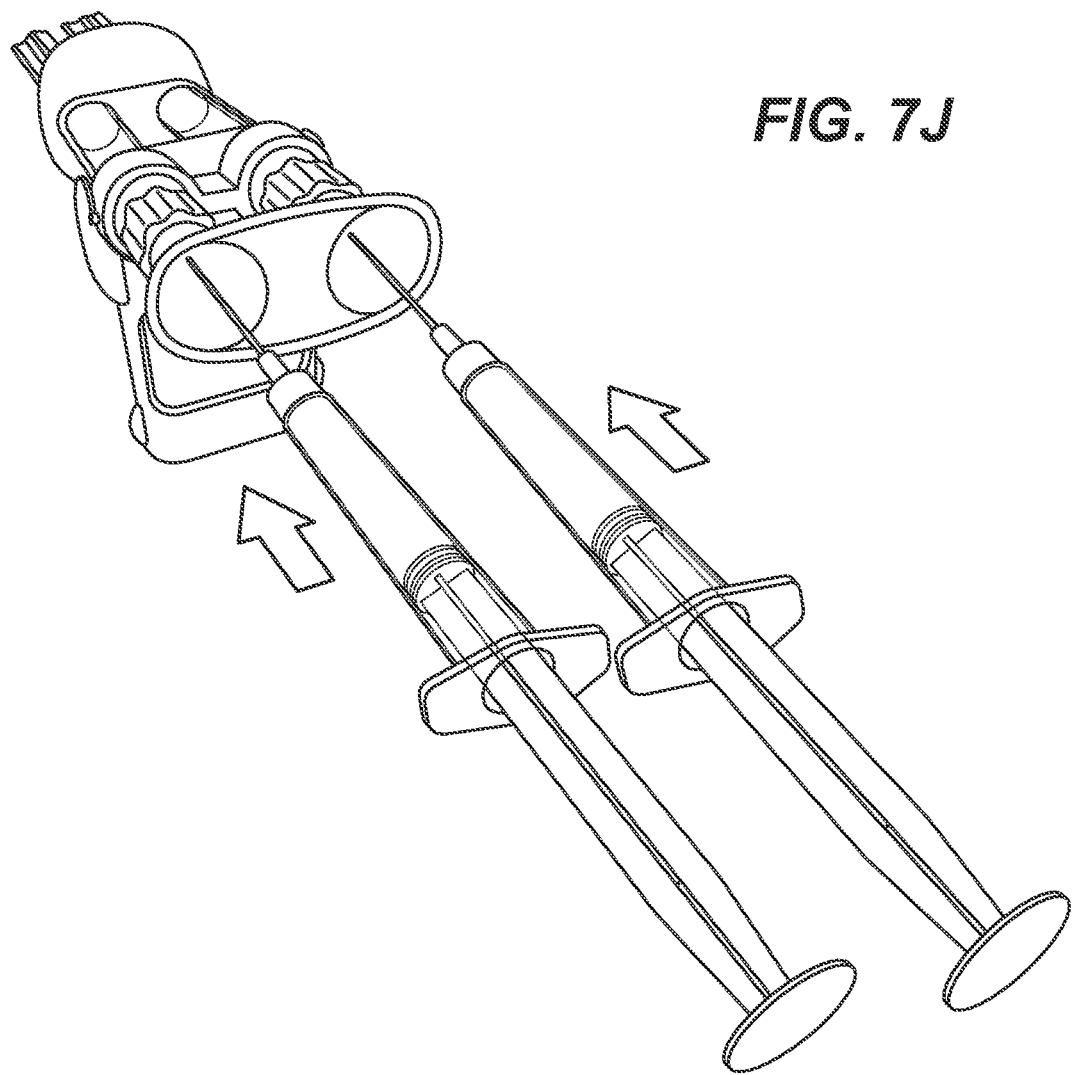
Figure 7K:
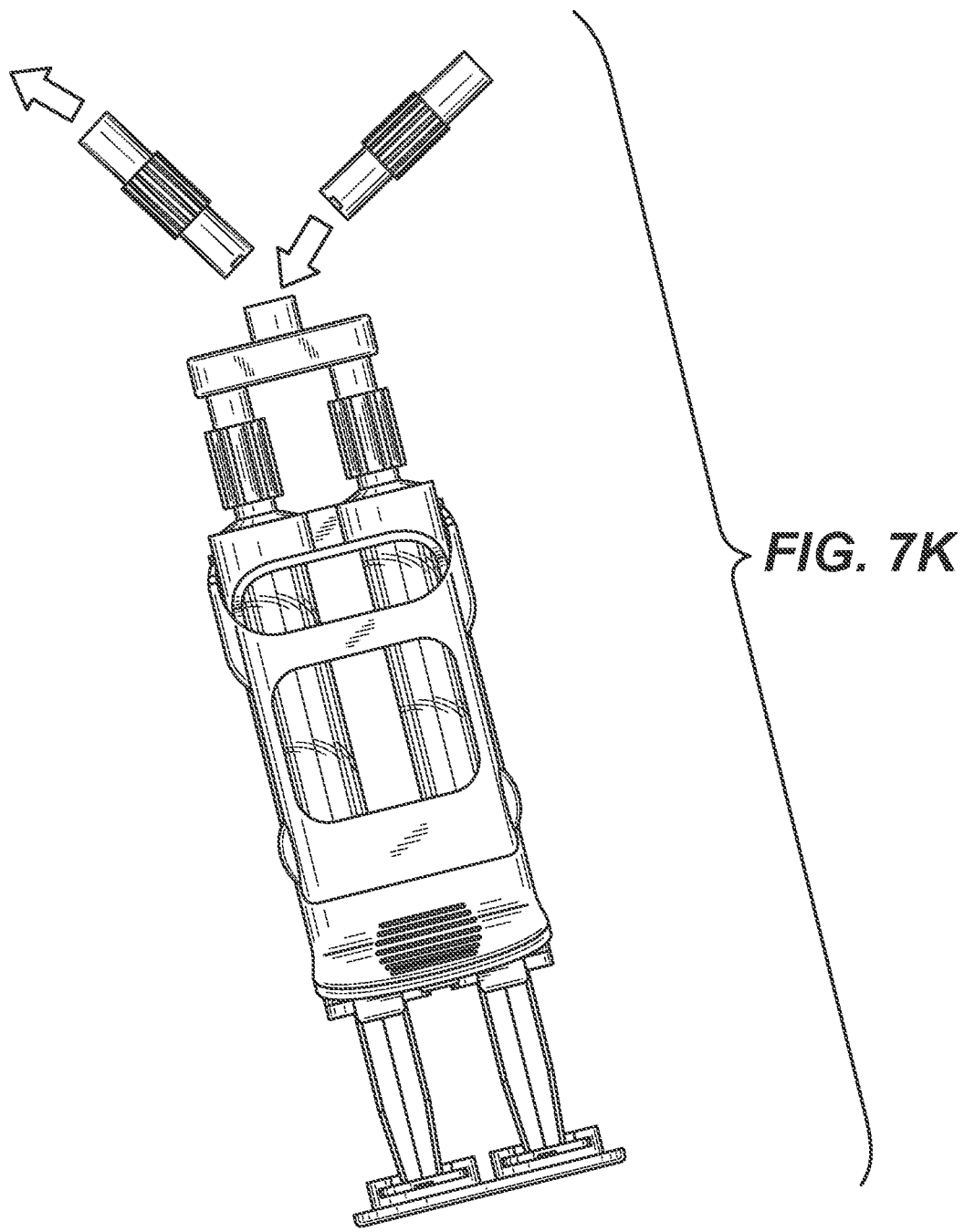
Figure 7L:
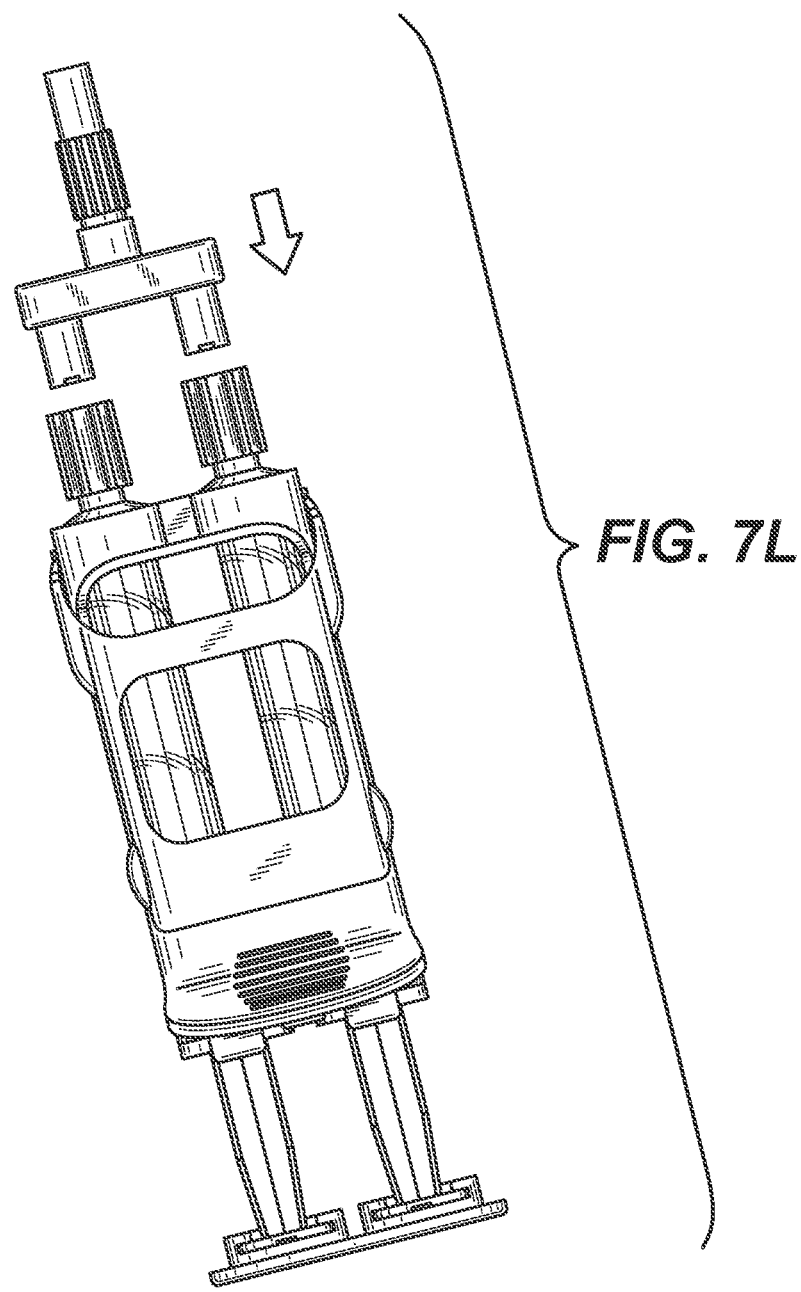
Figure 7M:
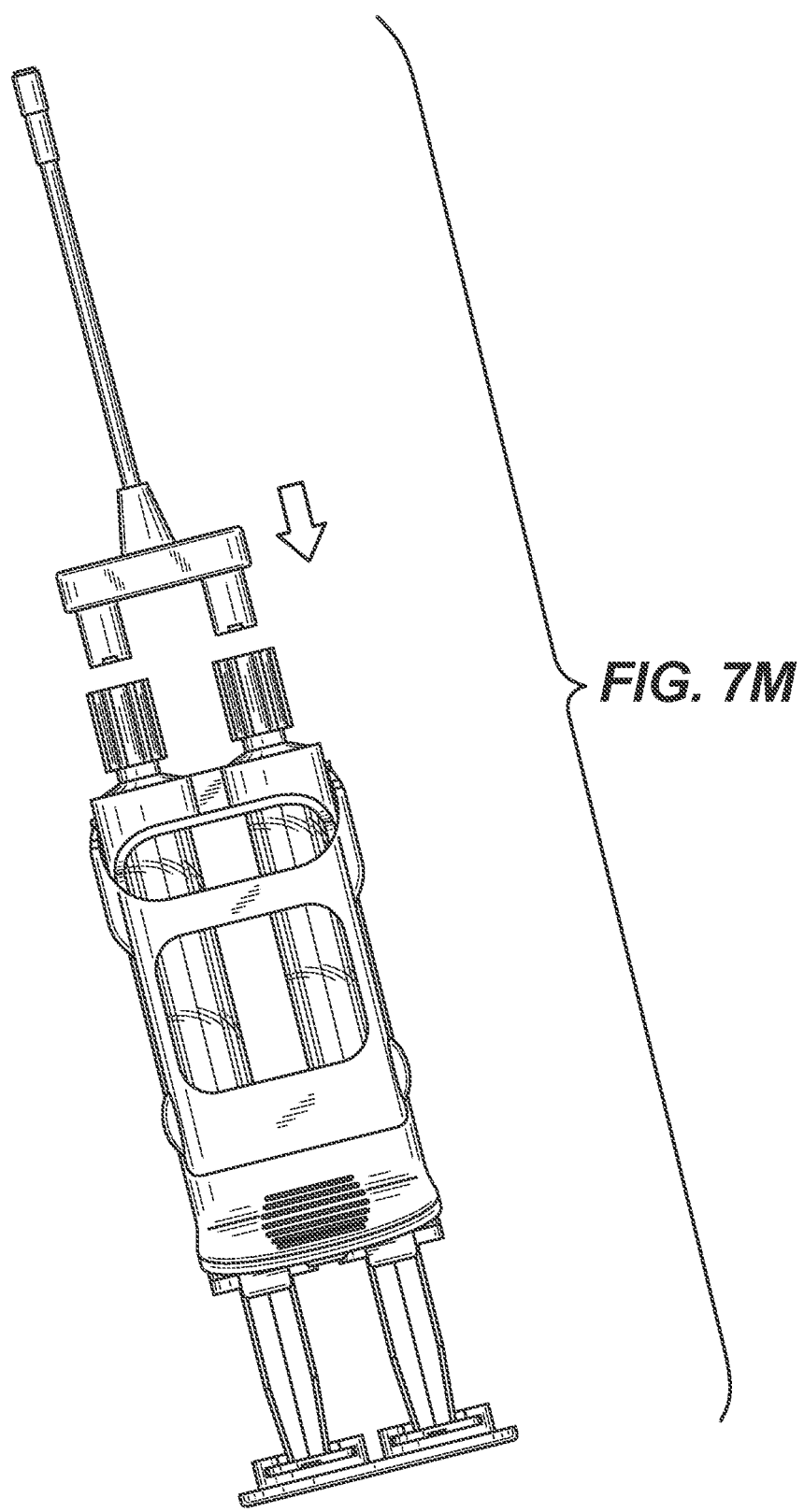
Figure 7N:
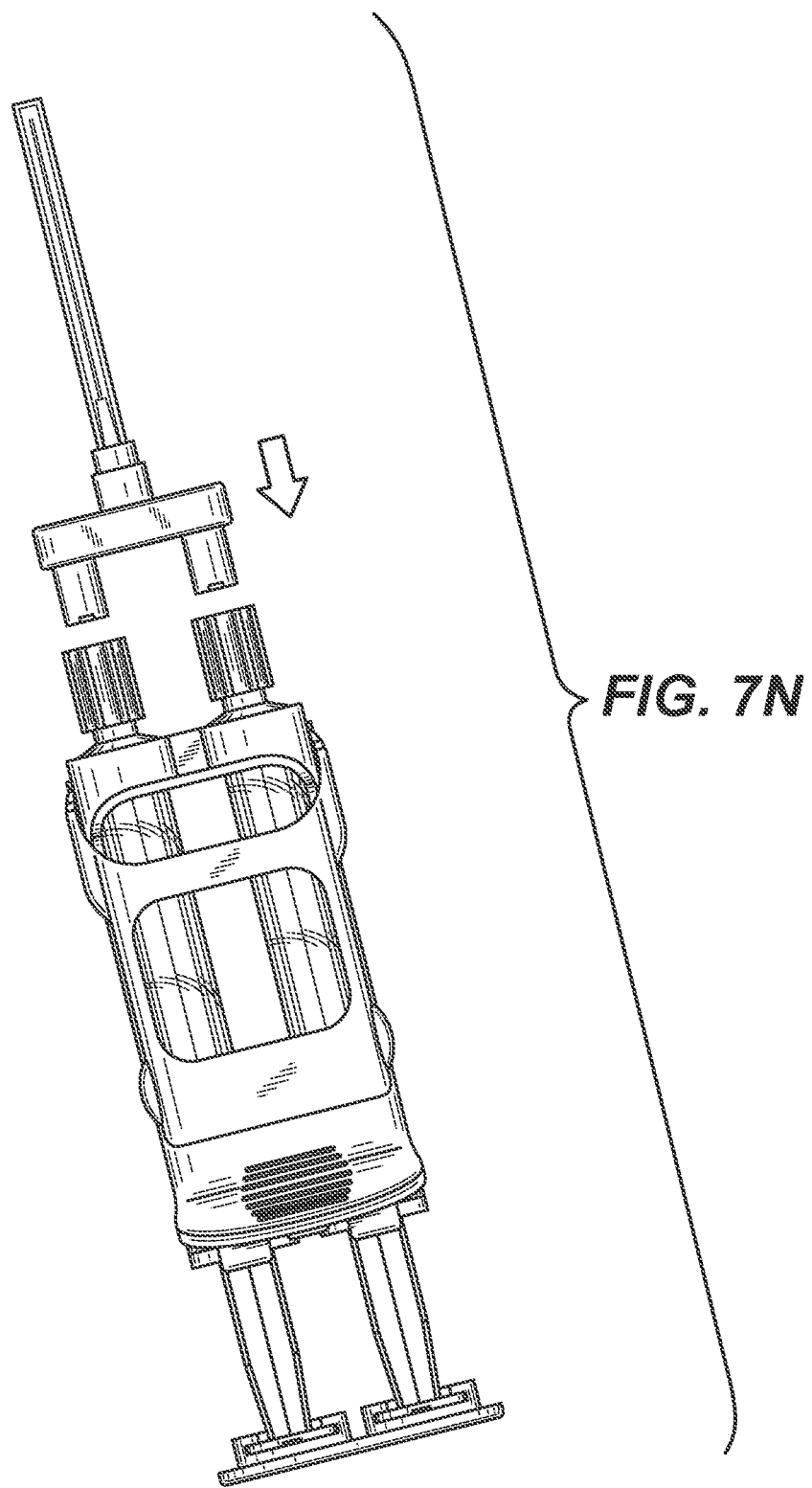
Figure 70:
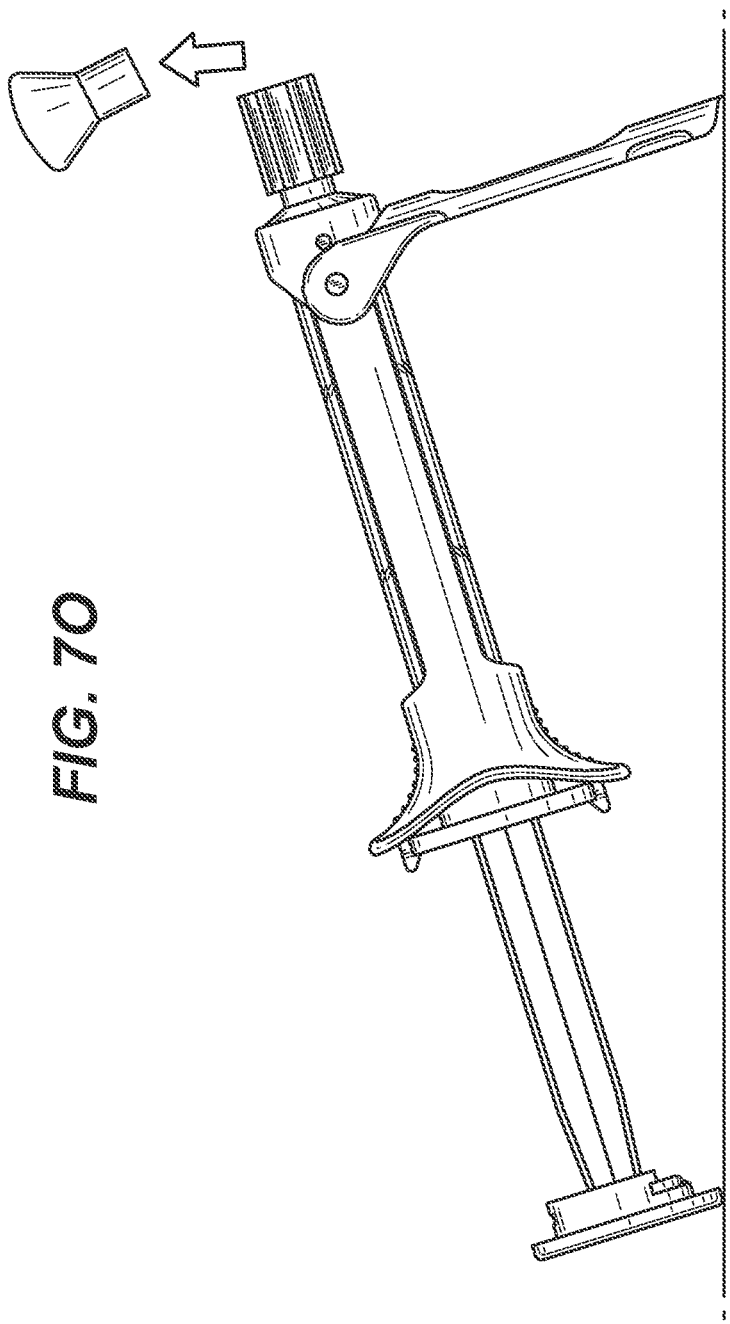

Device 10 is shown in the loading configuration in FIGS. 2-4 and in a drip configuration in FIGS. 5 and 6. In either configuration, device 10 comprises two supply containers provided as commercially available syringes 12 for solutions of biologic agents, such as proteins, such as fibrinogen, and of fibrinogen activators, such as thrombin, of a two-component tissue glue. Each syringe 12 comprises a hollow cylindrical syringe body 14 having a front end 16 with ports 18 and connecting pieces 90, and an open rear end 22 (not shown). Arranged in each syringe body 14 is a piston or plunger 24 in sealing abutment on the inner surface of syringe body 14. Piston 24 is held by a piston rod 26 guided out of syringe body 14 through the rear end 22. The piston rods 26 extend respectively in the longitudinal direction of the syringe bodies 14 and beyond open rear end 22. The free ends 30 of piston rods 26 facing away from piston 24 have annular flanges 32 formed thereon. These annular flanges 32 are mechanically connected to each other by a connecting element 34. Connecting element 34 is formed with two receiving recesses 36 which are laterally open and suited for insertion of the annular flanges 32 thereinto. The two syringe bodies 14 are connected to each other by a clip holding means 38 (hereinbelow referred to as a holding element). The bottom portion 16 of each syringe 12 includes a substantially flat, bottom surface that includes openings to left and right cavities. The left and right cavities are separated from each other and include tapered sidewalls which form frusto-conical cavities. The left inlet port is in fluid communication with the left outlet port with a left through bore. The right inlet port is in fluid communication with the right outlet port with a right through bore.

In one alternative loading configuration, particularly as shown in FIGS. 3 and 4, device 10 includes a deployed kick stand 80 and attached funnel 100. Funnel 100 is a dual funnel with two conical openings 110, 120 joined by connection portion 115 and configured for attachment to both syringes 14 simultaneously. Conical openings 110, 120 align to ports 18. Nuts 90 are configured to releasably attach funnel 100 to the ports. In one embodiment, funnel 100 is attached by a press fit to an outside surface corresponding to the tapered interior surface on each syringe 14, rather than by locking via a screw and/or luer nuts. For initial liquid transfer into each syringe 14, vial spike adaptors 15 from each reconstitution syringe 11 are replaced with blunt soft cannula 8. Cannulas 8 are used to deliver the liquids into the delivery device syringe though opening 110, 120 corresponding to each syringe 14. Dual conical funnel 100 provides larger target for cannula placement. Each conical opening 110, 120 channels cannula 8 and liquids into each barrel of syringe 14. Blunt tipped soft cannula 8, particularly when used in association with funnel 100, provide a safer, easier and faster means of delivering the liquids into device 10.

It is to be understood that any type of tips, including mixing tips, mixing spray tips, mixing drip tips, air-assist, airless spray, etc. tips can be used in accordance with the present inventive embodiments. While some drawings show drip tips and other show spray tips, any tips for mixing and expression of two components can be utilized in the present systems.

In one alternative drip configuration, as show in in FIGS. 5 and 6, device 10 includes a manifold 60 includes a substantially Y-shaped member having a first and a second proximal extension 62, 64 and a distal extension 66. Proximal extensions 62, 64 are configured for operable engagement with a first and a second source of component, e.g., syringes 14. Distal extension 66 is configured for operable engagement with elongated shaft 68, as will be discussed in further detail below. Manifold 60 further includes first and second component channels (not shown). First and second component channels fluidly communicate the first and second sources of components with a first and a second lumen 73, 75 (not shown) formed in elongated shaft 68. While manifold 60, as shown, is configured to receive only two sources of component, it is envisioned that manifold 60 may be configured to receive more than two sources of biological/medicinal components. Nuts 90 are configured to attach and secure manifold 60 to inlet ports 18.

Elongated shaft 68 may define a substantially solid body of silicone, plastic, polymer or other flexible material. As noted above, elongated shaft 68 includes first and second component lumens 73, 75 extending the length thereof. A wire (not shown) composed of a malleable material can also extend the length of elongated shaft 68. Wire 76 can maintain elongated shaft 68 in a bent or flexed configuration after elongated shaft 68 has been bent or flexed to accommodate a given procedure. Elongated shaft 68 is secured to distal extension 66 of manifold 60 such that first and second component lumens 73, 75 align with first and second component channels. Alternatively, elongated shaft 68 may be integrally formed at a distal end of manifold 60. As shown in FIGS. 2A, 5, 6, device 10 can be used with manifold 60 connected to elongated shaft 68 terminating with spray or drip tip 70, or alternatively tip 70 can be attached directly to manifold 60 with no elongated shaft 68.

FIG. 7 illustrates the primary steps required for transferring of liquid components into delivery device 10 and then conversion from a loading configuration to a dispensing or spray configuration. To begin, a first syringe 11 with a vial adaptor 15 is caused to pierce top barrier layer in storage vial 13(3), which contains a reconstituting solution, and to withdraw the liquid therein in conventional fashion. Storage vial 13(3) is replaced on the end of first syringe 11 with storage vial (1), which preferably contains, for example, fibrinogen in substantially solid form. The reconstituting solution is dispensed into storage vial (1) to dissolve the material therein. The reconstituted liquid is then drawn back into first syringe 11 and vial adaptor 15 is replaced with a first cannula 8. These steps are repeated in a second syringe 11 using storage vials (2) and (4) and a second cannula 8. In either or both instances, the reconstitution process can be accelerated with agitation and mild heat.

For loading purposes, kick stand 80 is deployed on device 10 by rotating about 90 degrees and by pulling (or retracting) the syringe plungers 30 to a predetermined position. Stand 80 elevates the inlets of syringes 14 relative to plunger handle 30 which allows reconstituted liquids to flow fully into each syringe 14. To prevent stand 80 from swinging shut, detents can be provided to lock it in the open or closed position. Once the reconstituted liquids have been transferred into each syringe 14 of device 10, kick stand 80 is rotated into a locked spray position, preferably using detents or other securement means, on device 10. Funnel 100 is removed and replaced with manifold 60 and the associated spray tip elements. Device 10 can now be utilized to spray multi-liquid components, particularly dual component formulations, such as fibrinogen and thrombin, in conventional fashion.

We claim:
1. A multi-liquid loading and delivery kit comprising:
a) a first storage vessel for a first active component; b) a second storage vessel for a second active component; c) at least two transfer syringes; d) at least two vial adaptors; e) at least two cannulas with a through lumen; and f) a multi-liquid delivery device comprising:
   a. dual hollow cartridges, each with at least one throughbore at one end and plunger access at an opposing end;
   b. a rotatable kick stand;
   c. a removable dual feed funnel;
   d. a spray manifold; and
   e. at least one spray tip assembly or drip tip assembly, wherein the removable dual feed funnel is interchangeable with the spray manifold.

2. The kit according to claim 1, wherein each cannula is flexible and is provided with a blunt non-traumatic end tip.

3. The kit according to claim 1, wherein the at least one drip tip assembly comprises a drip cartridge with a dual path opening in fluid communication via channels with a flexible drip outlet.

4. The kit according to claim 1, wherein the at least one spray tip assembly is directly attached to the spray manifold.

5. The kit according to claim 1, wherein the at least one spray tip assembly comprises a spray cartridge with a dual path opening, an interior mixing region, an atomizing insert and flexible spray outlet cover.

6. The kit according to claim 5, wherein the at least one spray tip assembly is connected via a multi-lumen, flexible tube to the spray manifold.

7. The kit according to claim 1, wherein the first and second active components are in solid form.

8. The kit according to claim 7, wherein at least the first active component is lyophilized powder.

9. The kit according to claim 1, wherein the first active component is thrombin and the second active component is a hemostatically active extract from blood plasma.

10. The kit according to claim 9, wherein the second active component is fibrinogen.

11. The kit according to claim 1 further comprising at least one reconstituting vessel containing a solubilizing liquid.

12. The kit according to claim 11, wherein the solubilizing liquid is an aqueous solution.

13. The kit according to claim 11, wherein the solubilizing liquid is a buffered solution containing a calcium salt.

14. A method of using the kit according to claim 1, comprising:
  a) placing a reconstitution set on a table,
  b) transferring the multi-liquid delivery device from the kit into a sterile field,
  c) preparing a first solution by:
    1) inserting a first vial adaptor of the at least two vial adaptors with a first syringe from the reconstitution set into a vial of a first dissolving solution,
    2) drawing the first dissolving solution into the first syringe,
    3) replacing the vial of the first dissolving solution on the first vial adaptor with a first active vial,
    4) injecting the first dissolving solution into the first active vial, thereby making a first active containing solution,
    5) withdrawing the first active containing solution into the first syringe, and
    6) replacing the first vial adaptor with a first cannula of the at least two cannulas,
  d) preparing a second solution by:
    1) inserting a second vial adaptor of the at least two vial adaptors with a second syringe from the reconstitution set into a vial of a second dissolving solution,
    2) drawing the second dissolving solution into the second syringe,
    3) inserting the second vial adaptor into a second actives vial,
    4) injecting the second dissolving solution into the second actives vial, thereby making a second active containing solution,
    5) withdrawing the second active containing solution into the second syringe,
    6) replacing the second vial adaptor with a second cannula of the at least two cannulas,
  e) retracting plungers of the first and second syringes to a predetermined position,
  f) rotating the kick stand into an open position,
  g) inserting one of the first cannula or the second cannula of the at least two cannulas through first and second funnels of the removable dual feed funnel of a barrel for each hollow cartridge in the multi-liquid delivery device,
  h) replacing the removable dual feed funnel with the spray manifold,
  i) attaching the at least one spray tip assembly or drip tip assembly to the spray manifold.

* * * * *